United States Patent
Yamaguchi

(10) Patent No.: US 7,534,886 B2
(45) Date of Patent: May 19, 2009

(54) FLUORINE-CONTAINING AMIDE COMPOUND AND METHOD FOR PREPARING THE SAME

(75) Inventor: Koichi Yamaguchi, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 175 days.

(21) Appl. No.: 11/445,277

(22) Filed: Jun. 2, 2006

(65) Prior Publication Data

US 2006/0276648 A1 Dec. 7, 2006

(30) Foreign Application Priority Data

Jun. 3, 2005 (JP) ............................... 2005-164397

(51) Int. Cl.
C07D 241/04 (2006.01)
C07D 295/00 (2006.01)

(52) U.S. Cl. ..................................... 544/358

(58) Field of Classification Search ........................ None
See application file for complete search history.

(56) References Cited

U.S. PATENT DOCUMENTS 6,111,050 A 8/2000 Yamaguchi et al.
6,114,528 A 9/2000 Yamaguchi et al.

FOREIGN PATENT DOCUMENTS

JP 11-92547 A 8/1989
JP 11-92557 A 8/1989

OTHER PUBLICATIONS

Gao et al. Journal of Polymer Science Part A: Plymer Chemistry, 2002, vol. 40, p. 2340-49.*
Koufaki et al., Bioorganic & Medicinal Chemistry, vol. 12, pp. 4835-4841, (2004).

* cited by examiner

*Primary Examiner*—James O. Wilson
*Assistant Examiner*—Noble Jarrell
(74) *Attorney, Agent, or Firm*—Birch, Stewart, Kolasch & Birch, LLP

(57) ABSTRACT

A fluorine-containing amide compound represented by the following formula (1):

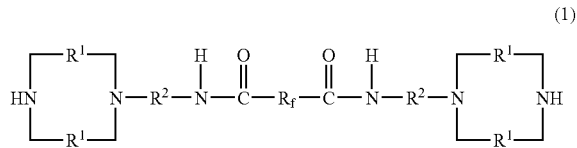

wherein $R_f$ is a divalent perfluoropolyether group, and each of $R^1$ and $R^2$ is a substituted or unsubstituted divalent hydrocarbon group, which may be the same with or different from each other.

5 Claims, 2 Drawing Sheets

FLUORINE-CONTAINING AMIDE COMPOUND AND METHOD FOR PREPARING THE SAME

CROSS REFERENCES

This application claims benefits of Japanese Patent application No. 2005-164397 filed on Jun. 3, 2005, the contents of which are hereby incorporated by reference.

FIELD OF THE INVENTION

The present invention relates to a fluorine-containing amide compound, specifically to a fluorine-containing amide compound which has improved reactivity with a specific molecular structure and is useful as a component of a composition such as a solvent resistant and chemical resistant rubber composition, a releasing agent composition or a water repellent composition. The present invention relates also to a method for preparing the amide compound.

DESCRIPTION OF THE PRIOR ART

Fluorine-containing compounds have been used for many applications. For example, a fluorine-containing elastomer obtained by crosslinking a polymer of a fluorine-containing compound, and a cured product of a fluorine-containing resin obtained by reacting a fluorine-containing compound with a curing agent are used as rubber materials, coating materials, releasing agents or water repellent agents.

However, many conventional fluorinated elastomers and cured products are not sufficiently solvent resistant or chemical resistance. Therefore, improvements in the solvent and chemical resistances have been desired. Particularly, improvement of releasing property and water repellency has been desired for coating, releasing and water repellent applications.

Japanese patent application laid-open No.11-92557 of the present assignee discloses the following fluorine-containing compound which gives an elastomer having improved solvent resistance, chemical resistance and releasing property:

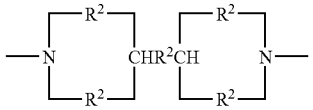

wherein $R_f$ is a divalent perfluoropolyether group, a is an integer of 0 or larger and, X is a group represented by the following formula (i), (ii) or (iii):

(i)

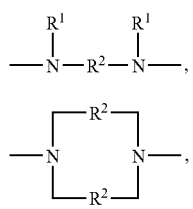

(ii)

(iii)

$$\begin{array}{c}\text{—N}\begin{bmatrix}\text{—R}^2\text{—}\\ \text{—R}^2\text{—}\end{bmatrix}\text{CHR}^2\text{CH}\begin{bmatrix}\text{—R}^2\text{—}\\ \text{—R}^2\text{—}\end{bmatrix}\text{N—}\end{array}$$

wherein each $R^1$ is an alkyl, cycloalkyl, aryl, aralkyl group or a partly or fully halogenated group thereof, each having 1 to 12 carbon atoms, and each $R^2$ is an alkylene, cycloalkylene, arylene group or a partly or fully halogenated group thereof, each having 1 to 10 carbon atoms.

Further, Japanese Patent Application Laid-open No.11-92547 of the present assignee discloses a composition comprising the aforesaid fluorine-containing amide compound, and a fluorine-containing epoxy compound or a fluorine-containing isocyanate compound, which composition is useful for preparing a rubber or a releasing agent.

However, the reaction between aforesaid amide compound with the epoxy or the isocyanate compound is very slow to take from one to a few days at room temperature to complete.

The object of the present invention is to provide a fluorine-containing amide compound which has improved reactivity and gives a fluorine-containing elastomer or cured product having an excellent solvent resistance, chemical resistance, releasing property, and water repellency.

SUMMARY OF THE INVENTION

The present inventor has found that the above object can be attained by a fluorine-containing amide compound having an active hydrogen atom at a specific position. The present invention is a fluorine-containing amide compound represented by the following formula (1):

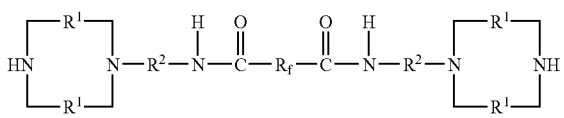

(1)

wherein $R_f$ is a divalent perfluoropolyether group, and each of $R^1$ and $R^2$ is a substituted or unsubstituted divalent hydrocarbon group, which may be the same with or different from each other.

The present invention is a method for preparing the above amide compound comprising the step of reacting a diester compound with an amine compound.

The fluorine-containing amide compound of the present invention has improved reactivity and gives a cured product having excellent solvent resistance and chemical resistance. The present method can produce the fluorine-containing amide compound efficiently.

DESCRIPTION OF THE PREFERRED EMBODIMENTS

Figure 1:
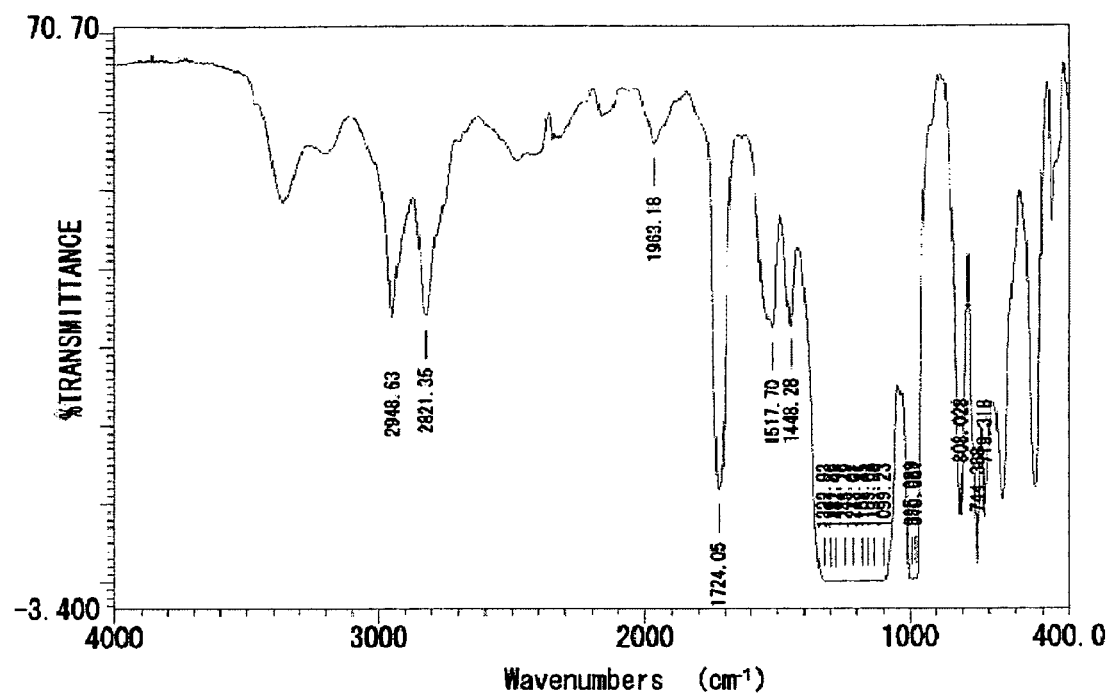
FIG. 1 shows an IR spectrum of the amide compound prepared in Example 1.

In the formula (1), $R_f$ is a divalent perfluoropolyether group. Examples of a polyether moiety of the perfluoropolyether group include various divalent residues of polymers having an ether bond, —O—, such as polyethylene oxide (EEO), polypropylene oxide (PPO), polyethylene-polypropylene copolymer, polyethylene glycol polyalkyl ether and polyethylene glycol polyphenyl ether. $R_f$ is a group in which fluorine atoms substitute for all of the hydrogen atoms of these residues.

Preferably, $R_f$ has a divalent saturated perfluoropolyether moiety represented by the compositional formula, $C_hF_{2h}O$, wherein h is an integer of from 1 to 6, preferably from 1 to 3. The moiety may have a branched structure.

Preferably, the aforesaid divalent saturated perfluoropolyether moiety is represented by the following formula (i) or (ii):

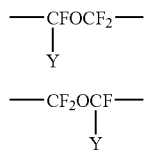

(i)

(ii)

wherein Y is a fluorine atom or a $CF_3$ group.

Preferably, $R_f$ has a total of 2 to 200, more preferably 2 to 100, moieties of the formulas (i) and (ii). For example, $R_f$ is represented by the following formula:

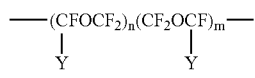

wherein Y is as defined above, m and n each is an integer of 1 or larger with the proviso that m+n ranges from 2 to 200, preferably from 1 to 100.

The above formula can be expressed as follows:

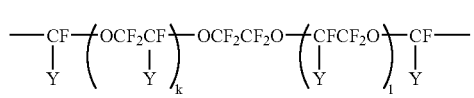

wherein k corresponds to n−1 and l to m−1 in the aforesaid formula.

$R_f$ may have another moieties to be represented by the following formula (A), (B), (C) or (D), for instance:

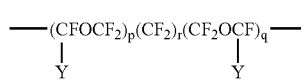

(A)

wherein Y is as defined above, p and q each is an integer of 1 or larger, with the proviso that p+q ranges from 2 to 200, preferably from 2 to 100, and r is an integer of from 0 to 6;

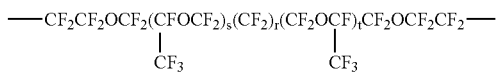

(B)

wherein r is as defined above, s and t each is an integer of 0 or larger, with the proviso that s+t ranges from 0 to 200, preferably from 2 to 100;

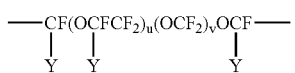

(C)

Y is as defined above, u and v each is an integer of from 1 to 100; and

(D)

wherein w is an integer of from 1 to 100.

Examples of $R_f$ represented by the aforesaid (A), (B), (C) or (D) are as shown below:

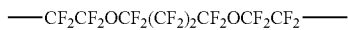

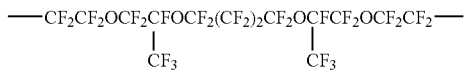

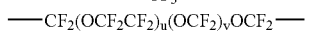

wherein u is an integer of from 5 to 100, and v is an integer of from 1 to 100;

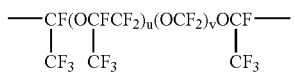

wherein u is an integer of from 5 to 100, and v is an integer of from 1 to 100; and

wherein w is an integer of from 5 to 100.

$R_f$ may be a mixture of the aforesaid groups or a mixture of the groups of the same formula but with different values of the parameters, for example n, in the specified ranges. In practice, $R_f$ is defined with an averaged value of each parameter.

In the formula (1), each of $R^1$ and $R^2$ is a substituted or unsubstituted divalent hydrocarbon group having 1 to 10 carbons, preferably 2 to 6 carbons. In the formula (1), $R^1$ and $R^2$ may be the same with or different from each other, four $R^1$'s may be the same with or different from each other and two $R^2$'s may be the same with or different from each other. Examples of $R^1$ and $R^2$ include alkylene groups such as methylene, ethylene, n-propylene, i-propylene, butylene, and hexamethylene groups; cycloalkylene groups such as cyclohexylene group; arylene groups such as phenylene, tolylene, xylylene, naphthylene, and biphenylene groups; and partly or fully fluorinated groups thereof.

In the formula (1), $R^1$ and N atoms are directly bonded through a single bond to form a 4- to 22-membered ring, preferably 6- to 14-membered ring, depending on the number of carbon atoms in $R^1$.

The amide compound of the present invention is characterized in that it has both secondary amines and secondary amides. Compared with the amide compound described in Japanese patent application laid-open No.11-92557, the present amide compound has significantly larger reactivity with an epoxy group and an isocyanate group. Increased number of active hydrogen atoms may naturally increase reactivity. However, depending on locations of the active hydrogen atom, properties of a reaction product may be worsened. Further, too high reactivity may cause problems in handling or storage stability of an amide. Extensive studies by the present inventor have found that the amide compound of the present invention to have a higher reactivity to give a cured product having satisfactory the properties.

The present amide compound is in the form ranging from a polymer having a low viscosity of about 100 centistokes (cs) at 25° C. to a gummy or solid polymer having a viscosity of about 100,000 cs or higher. A polymer with a viscosity lower than the aforesaid lower limit may give a cured product having insufficient elongation. Preferably, a gummy polymer having a viscosity of 100,000 cs or higher is used for a hot-vulcanized rubber, and a polymer having a viscosity of from 100 to 100,000 cs is used for a liquid rubber, for instance. The viscosity can be adjusted by selecting each parameter of the aforesaid formulas representing $R_f$.

The present amide compound can be synthesized by the following method comprising the step of reacting a compound having ester groups at both ends represented by the following formula (2) with an amine compound represented by the following formula (3):

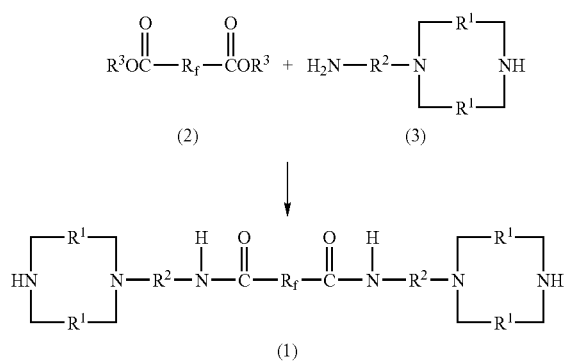

wherein each $R^3$ is an alkyl group having 1 to 5 carbon atoms, and $R_f$, $R^1$ and $R^2$ are as defined above.

Compared with a method using an acid halide as described in Japanese Patent Application Laid-open No.11-92547, the aforesaid method is superior in that a halogen acid such as hydrofluoric acid is not formed. In addition, a bi-product, i.e., an alcohol can be removed easily. Moreover, the secondary amino group in the formula (3) remains unreacted, while the primary amino group reacts selectively with the ester compound. The amine compound of the formula (3) has only one primary amino group, so that no thickening occurs due to chain extension.

In the above reaction, the ester compound of the formula (2) and the amine compound of the formula (3) are reacted in a molar ratio, (a)/(b), wherein (a) represents a molar amount of the ester compound and (b) represents that of the amine compound, of from 0.05 to 1 mol/mol, preferably from 0.1 to 0.5 mol/mol. Within the range of the molar ratio, the ester compound is surely modified at their ends to give an intended compound with a high yield.

Although the conditions of the above reaction are not critical, the reaction is typically carried out at a temperature of from 20 to 120° C. for 1 to 8 hours, preferably at a temperature of from 40 to 100° C. for 2 to 5 hours. Use may be made of an organic solvent in an amount not to adversely affect the reaction. Preferably, an organic solvent capable of dissolving or uniformly dispersing the reaction mixture is used for faster reaction. Examples of such organic solvent include hydrocarbon solvents such as hexane, cyclohexane, toluene, and xylene; ether solvents such as diethyl ether, n-butyl ether, dioxane, and tetrahydrofuran; ketone solvents such as acetone, methyl ethyl ketone, methyl isobutyl ketone and ethylacetate; chlorohydrocarbon solvents such as methylene chloride, chlorobenzene, and chloroform; nitrile solvents such as acetonitrile; and fluorinated solvents such as trifluorobenzene, 1,3-bistrifluoromethylbenzene, and perfluorooctane; and a mixture thereof.

The amide compound of the present invention has a high fluorine content. It can form an elastomer or a cured product which has low surface energy and can be used for various applications such as a solvent resistant and chemical resistant rubber material, a releasing agent, and a water repellent agent. An elastomer which is obtained by reacting the present amide compound with a compound having three or more epoxy groups per molecule, for example, is advantageously used as a sealant, a molded article, a coating agent, a releasing agent, or a water repellent agent.

EXAMPLES

The present invention will be further explained with reference to the following examples, but is not limited thereto. In the formulas shown below, Me means a methyl group.

Example 1

The ester compound of the following formula (4) in an amount of 500 g, and 500 g of 1,3-bistrifluoromethylbenzene were placed in a 2-liter four necked flask equipped with a stirrer, a thermometer, a Dimroth condenser, and a dropping funnel, and heated to a temperature of 70° C. while stirring.

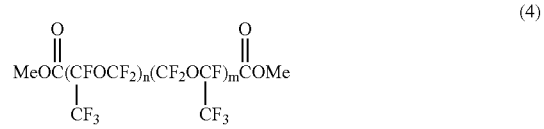

In the formula (4), an average of n+m is 39.

Subsequently, 24.5 g of 1-(2-aminoethyl)piperazine was added through the dropping funnel at a temperature of from 70 to 80° C. After the addition completed, the reaction mixture was heated to a temperature of 80° C. After keeping the reaction mixture at that temperature for 4 hours, water was added to extract methyl alcohol formed in the reaction and unreacted excess 1-(2-aminoethyl)piperazine. The organic phase was isolated and subjected to a distillation at a temperature of 100° C. and at a pressure of 3 mmHg to remove 1,3-bistrifluoromethylbenzene. A transparent light yellow liquid compound thus obtained weighed 477.8 g and had a viscosity of 25,690 cs at 25° C., and a refractive index of 1.315 at 25° C. FIG. 1 shows an IR spectrum of the compound in which the following absorption bands were observed.

| | |
|---|---|
| 1100-1350 cm$^{-1}$ | $\nu$C—F |
| 1724 cm$^{-1}$ | $\nu$C=O |

The compound was found to have an amine equivalent weight of 1695 g/mole and was identified to have the following structure of the formula (5):

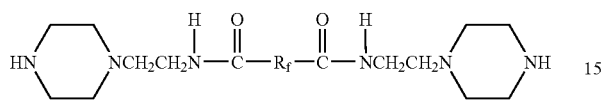

(5)

wherein $R_f$ is represented by the following formula with an average of n+m being 39.

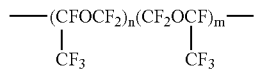

Example 2

Example 1 was repeated except that 500 g of the ester compound of the formula (6) shown below was used in place of the ester compound of the formula (4), and 9.9 g of 1-(2-aminoethyl)piperazine was used.

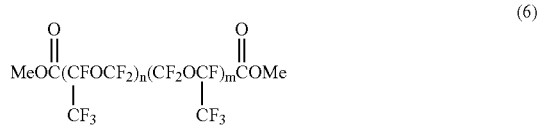

(6)

In the formula (6), an average of n+m is 97.

Figure 2:
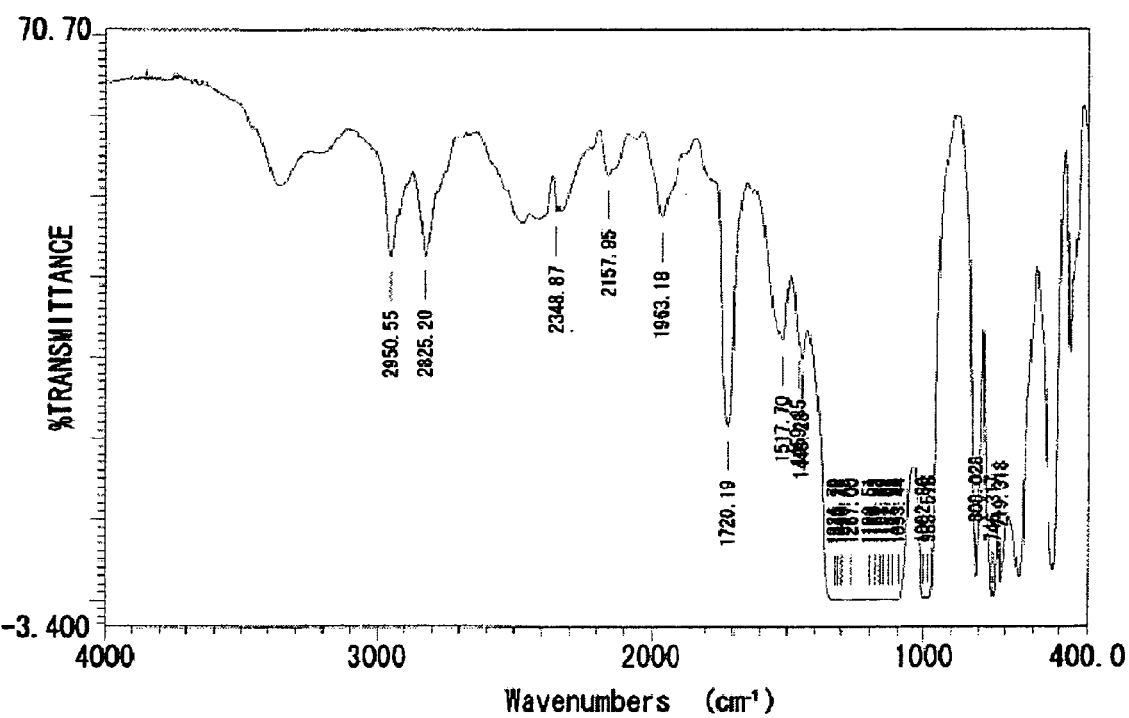
FIG. 2 shows an IR spectrum of the amide compound prepared in Example 2.

A transparent light yellow liquid compound thus obtained weighed 481.3 g and had a viscosity of 22,390 cs at 25° C., and a refractive index of 1.307 at 25° C. FIG. 2 shows an IR spectrum of the compound in which the following absorption bands were observed.

| | |
|---|---|
| 1100-1350 cm$^{-1}$ | $\nu$C—F |
| 1720 cm$^{-1}$ | $\nu$C=O |

The compound was found to have an amine equivalent weight of 4130 g/mole and was identified to have the following structure of the formula (7):

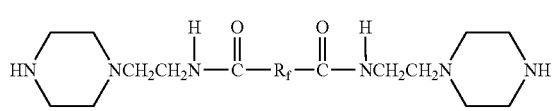

(7)

wherein $R_f$ is represented by the following formula with an average of n+m being 97.

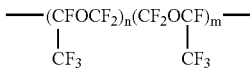

Comparative Example 1

The compound of the formula (8) below was prepared according to the method described in Japanese patent application laid-open No.11-92557.

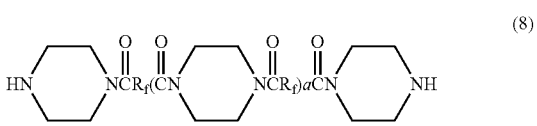

(8)

In the formula (8), an average of a is 0.88, and $R_f$ is represented by the following formula with an average of n+m being 37.

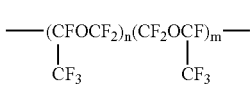

Evaluation of Curing Property

Figure 3:
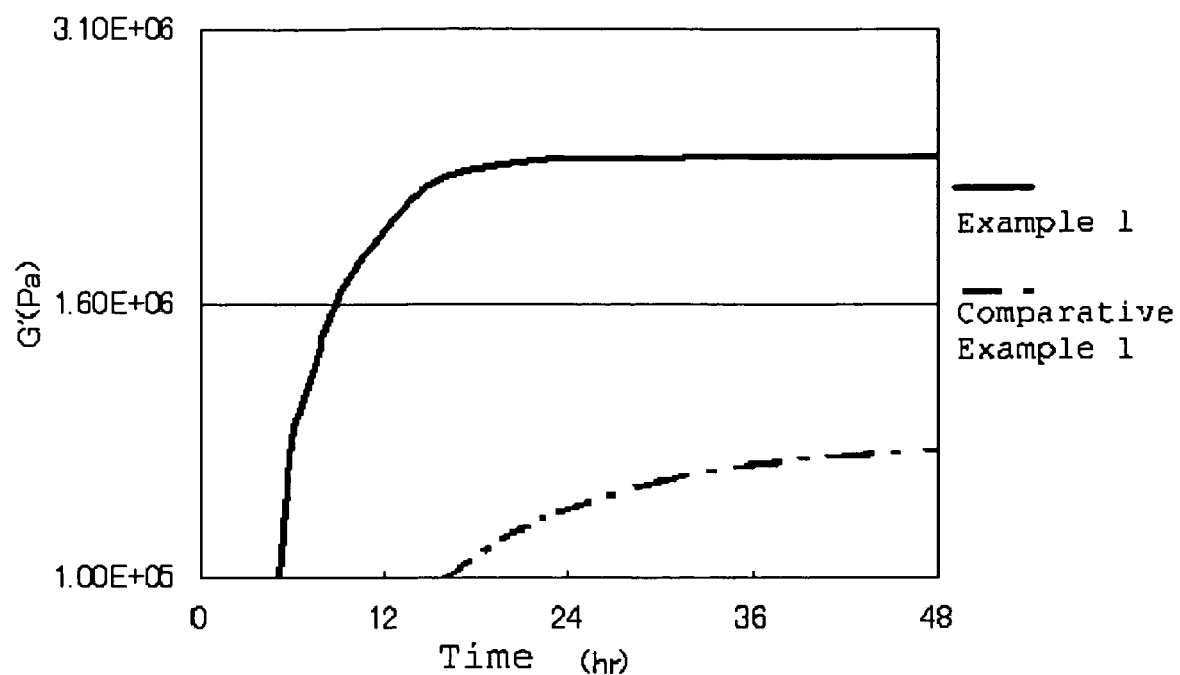
FIG. 3 shows storage elasticity moduli vs. time of the mixtures prepared in Example.

Curing property or reactivity at 25° C. was compared between the amide compounds prepared in Example 1 and in Comparative Example 1. One gram of each amide compound was mixed with a three-functional epoxy compound of the following formula (9), Epikote 630, ex Shell Chemicals Japan Ltd., in a mass ratio shown in Table 1. Change in storage elastic modulus with time was measured with a rheometer, Advanced Rheometric Expansion System (ARES), ex Rheometric Scientific Inc. FIG. 3 shows the storage elastic modulus vs. time, and Table 1 shows some physical properties of the cured products obtained. In Table 1, the cure time is a period of time required for each mixture to show no increase in the storage elastic modulus.

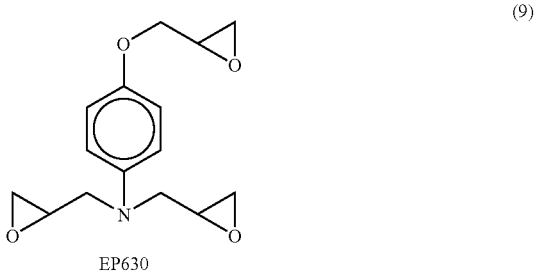

(9)

EP630

TABLE 1

| | | Example 1 | Comparative Example 1 | |
|---|---|---|---|---|
| Content, Parts by mass | Fluorine-containing amide compound | 100 | 100 | |
| | Epoxy compound | 2.4 | 3 | |
| Curing property | Cure time at 25° C., hr | 24 | 48 | 72 |

TABLE 1-continued

|  |  | Example 1 | Comparative Example 1 | |
|---|---|---|---|---|
| Properties of cured products | Hardness | 58 | 43 | 47 |
|  | Elongation, % | 309 | 616 | 407 |
|  | Tensile strength, MPa | 3.1 | 2.6 | 2.6 |

As shown in Table 1, the amide compound of the present invention reacts significantly faster than the amide compound of the Comparative Example. The storage elastic modulus of the cured product obtained in Comparative Example 1 kept increasing little by little with time, so that the physical properties were measured both at 48 hours and 72 hours after mixing.

The invention claimed is:

1. A fluorine-containing amide compound represented by the following formula:

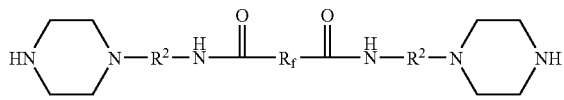

wherein $R_f$ is a divalent perfluoropolyether group, and $R^2$ is a member selected from the group consisting of ethylene, n-propylene, i-propylene, butylene, and hexamethylene.

2. The fluorine-containing amide compound according to claim 1, wherein $R_f$ has a divalent saturated perfluoropolyether moiety, which may be branched, represented by the compositional formula, $C_hF_{2h}O$, wherein h is an integer of from 1 to 6.

3. The fluorine-containing amide compound according to claim 2, wherein the saturated perfluoropolyether moiety is represented by the following formula (i) or (ii),

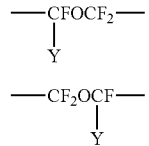

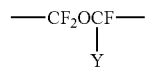

wherein Y is a fluorine atom or a $CF_3$ group.

4. The fluorine-containing amide compound according to claim 3, wherein $R_f$ has a total of 2 to 200 moieties of the formulas (i) and (ii).

5. A method for preparing the fluorine-containing amide compound according to any one of claims 1 to 4, comprising the step of reacting an ester compound of the following formula (2) with an amine compound of the following formula (3'):

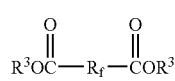

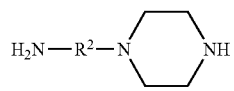

wherein each $R^3$, which may be the same with or different from each other, is an alkyl group having 1 to 5 carbon atoms, $R_f$ is a divalent perfluoropolyether group, and $R^2$ is a member selected from the group consisting of ethylene, n-propylene, i-propylene, butylene, and hexamethylene.

* * * * *